(12) United States Patent
Allen

(10) Patent No.: US 6,783,531 B2
(45) Date of Patent: Aug. 31, 2004

(54) COMPRESSION BONE STAPLE, APPARATUS AND METHOD

(75) Inventor: Drew Allen, San Jose, CA (US)

(73) Assignee: Drew Allen, DPM, San Jose, CA (US)

( * ) Notice: Subject to any disclaimer, the term of this patent is extended or adjusted under 35 U.S.C. 154(b) by 18 days.

(21) Appl. No.: 09/985,719

(22) Filed: Nov. 6, 2001

(65) Prior Publication Data

US 2002/0173793 A1 Nov. 21, 2002

Related U.S. Application Data

(63) Continuation of application No. 09/500,060, filed on Feb. 8, 2000, now Pat. No. 6,348,054, which is a continuation-in-part of application No. 09/299,285, filed on Apr. 26, 1999, now Pat. No. 6,059,787.

(51) Int. Cl.[7] ............................................. A61B 17/56
(52) U.S. Cl. ....................................................... 606/75
(58) Field of Search ........................ 606/75, 105, 151, 606/219, 220, 221; 411/457, 458, 460, 522, 920

(56) References Cited

U.S. PATENT DOCUMENTS

| | | | | |
|---|---|---|---|---|
| 709,392 A | * | 9/1902 | Brown | 606/221 |
| 816,026 A | * | 3/1906 | Meier | 606/221 |
| 2,231,178 A | * | 2/1941 | Beckwith | 411/474 |
| 2,309,536 A | * | 1/1943 | Reid et al. | 411/473 |
| 3,862,631 A | | 1/1975 | Austin | |
| 3,939,828 A | | 2/1976 | Mohr et al. | |
| 4,340,331 A | * | 7/1982 | Savino | 411/457 |
| 4,723,540 A | | 2/1988 | Gilmer, Jr. | |
| 4,838,254 A | | 6/1989 | Gauthier | |
| 4,994,063 A | | 2/1991 | Garner | |
| 5,007,921 A | | 4/1991 | Brown | |
| 5,026,390 A | | 6/1991 | Brown | |
| 5,242,457 A | * | 9/1993 | Akopov et al. | 606/144 |
| 5,246,443 A | | 9/1993 | Mai | |
| 5,634,926 A | * | 6/1997 | Jobe | 606/69 |
| 5,779,707 A | * | 7/1998 | Bertholet et al. | 606/75 |
| 5,785,713 A | | 7/1998 | Jobe | |
| 5,947,999 A | | 9/1999 | Groiso | |
| 6,325,805 B1 | * | 12/2001 | Ogilvie et al. | 606/75 |

* cited by examiner

Primary Examiner—Eduardo C. Robert
(74) Attorney, Agent, or Firm—Wilson Sonsini Goodrich & Rosati

(57) ABSTRACT

A method and apparatus for interosseous bone fixation uses a compression staple, generally U-shaped, having a pair of legs with sharp front ends and proximal ends interconnect by a bridge portion that is resilient and bowed, the staple having an initial configuration and capable of a tensioned configuration by spreading apart the legs by a certain amount causing the curvature of the bowed bridge to lessen and the legs urged towards each other with certain compressive spring force. A staple applicator supports and guides the staple and positions the tensioned staple with its pointed ends forward, adjacent an ejection port at the front of the applicator. A powered strike member is mounted for longitudinal movement and has a front end that will strike the rear of the tensioned staple with percussive force and eject it in tensioned configuration from the applicator.

2 Claims, 7 Drawing Sheets

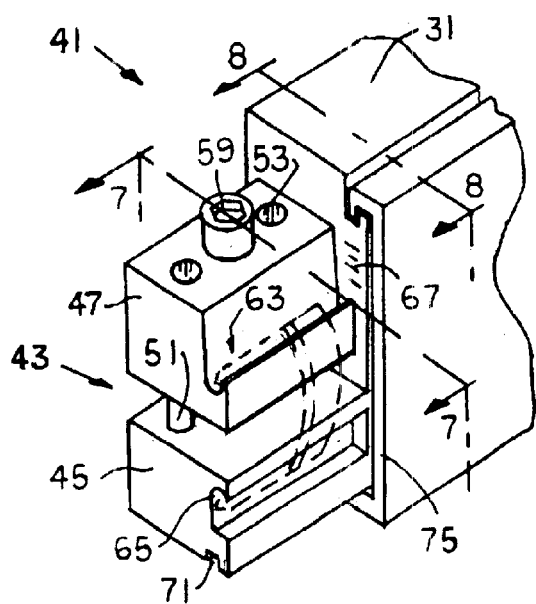
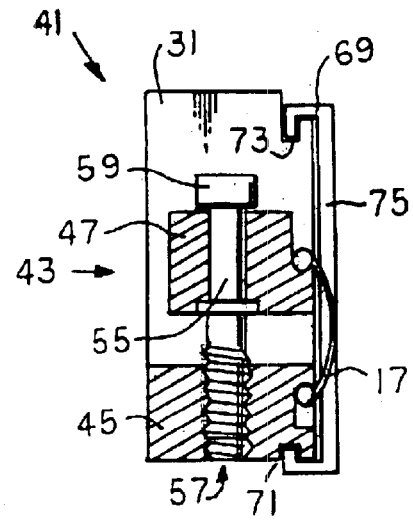
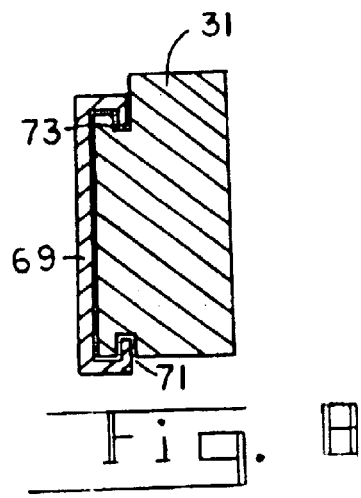
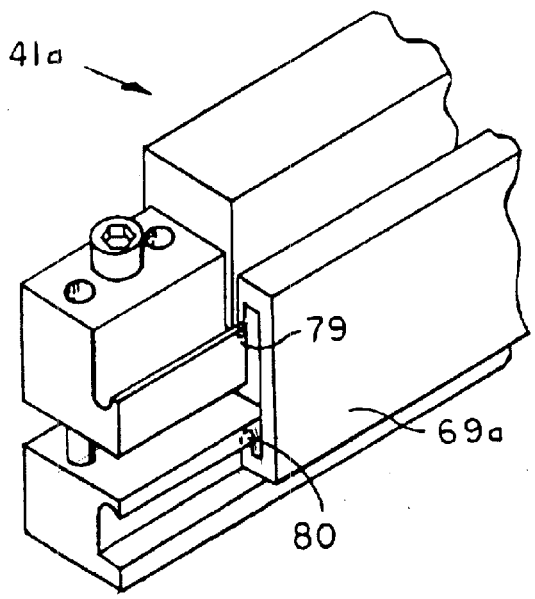

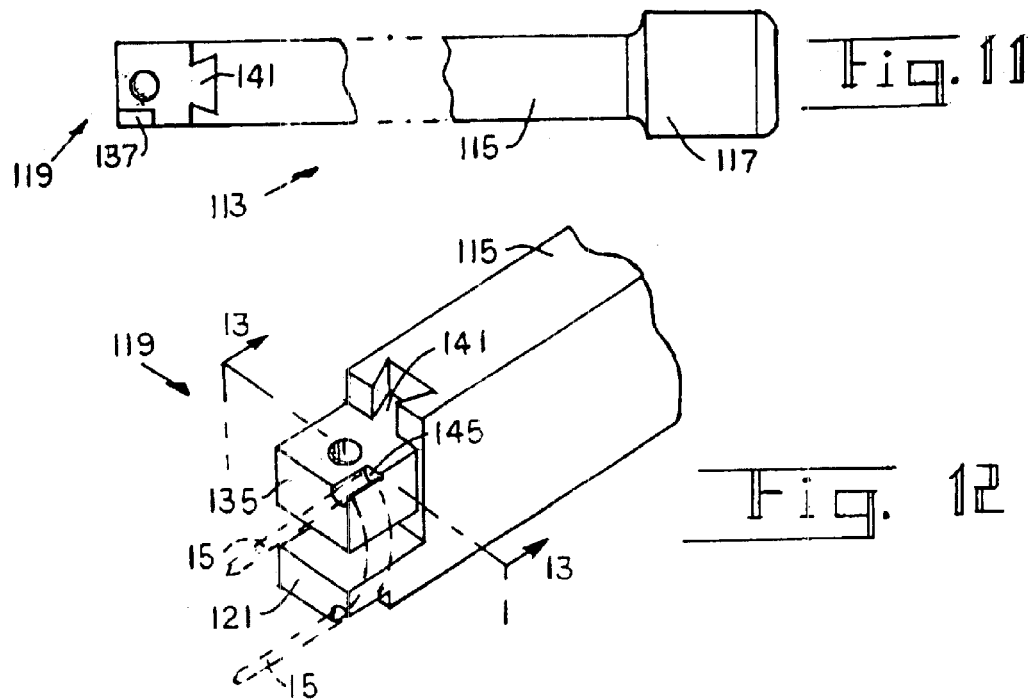
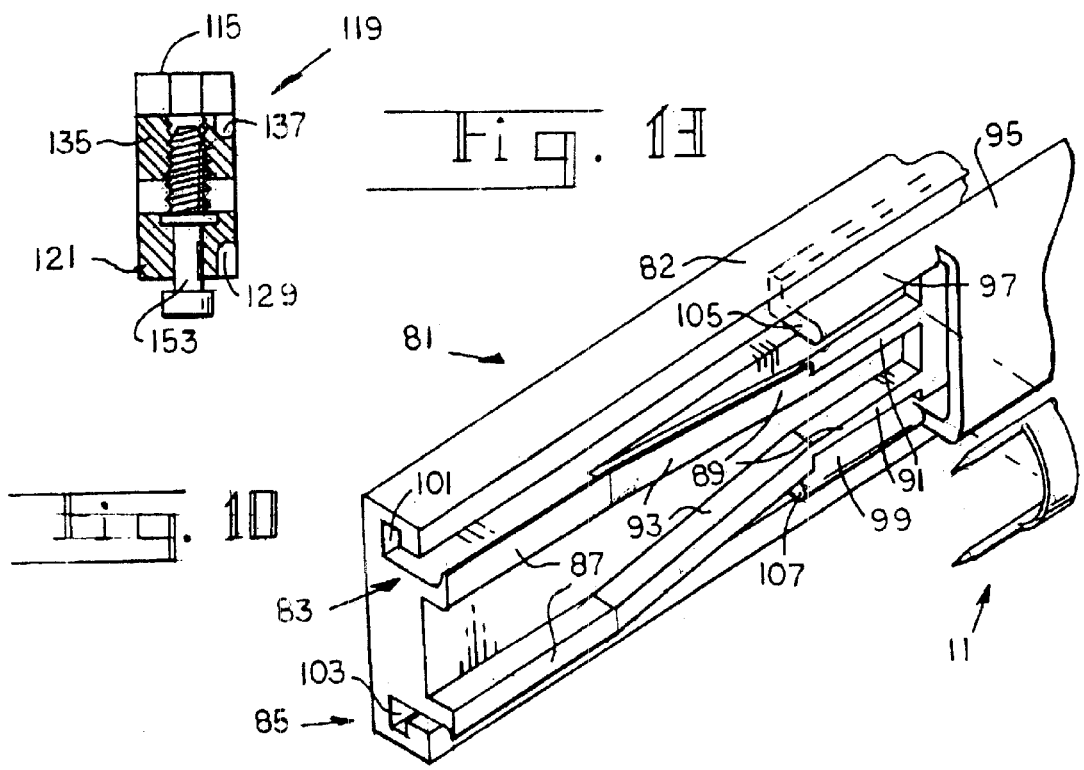

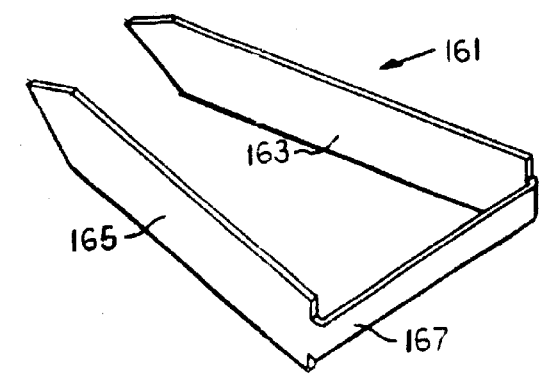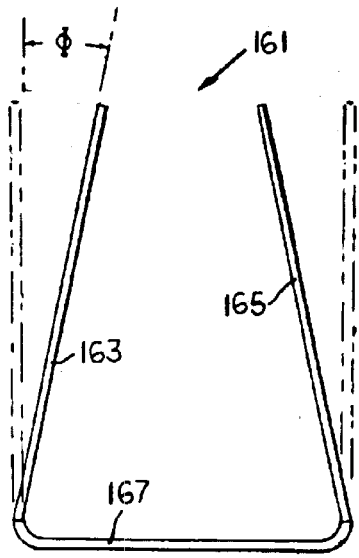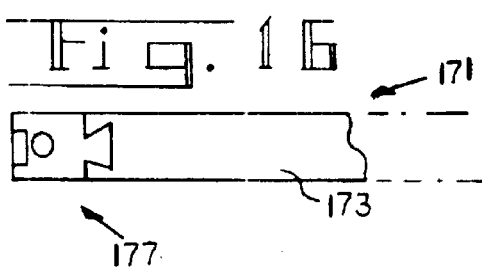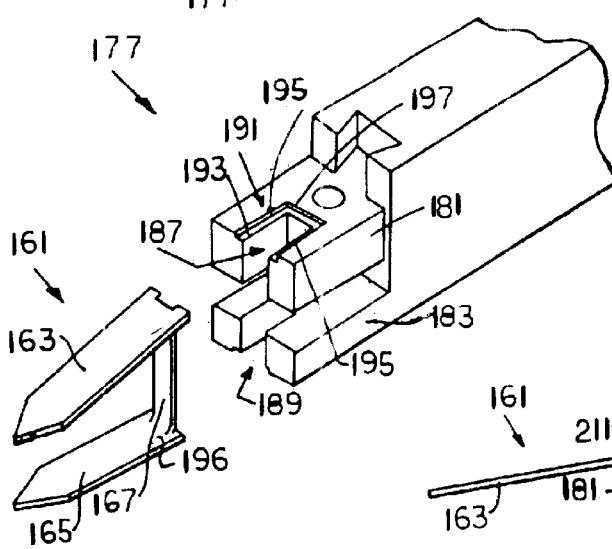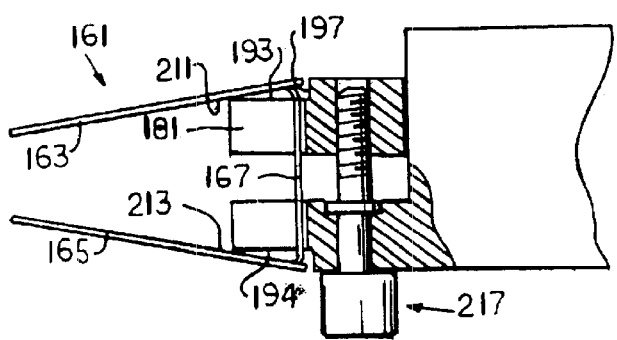

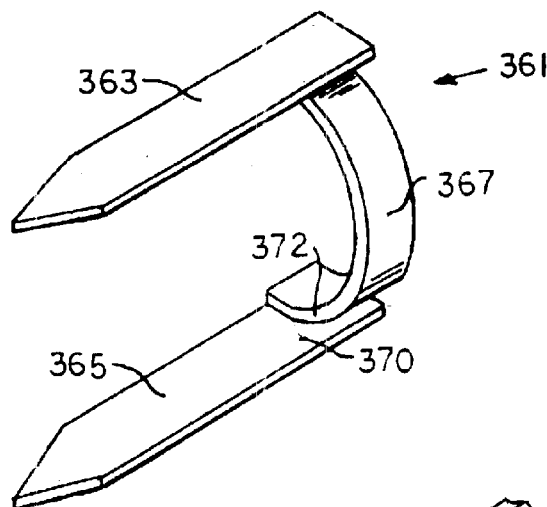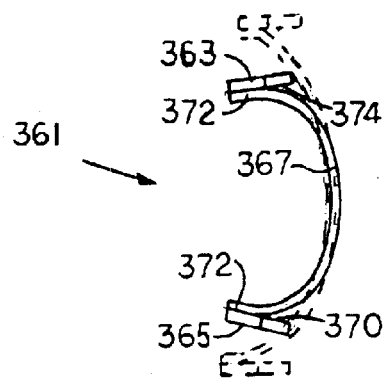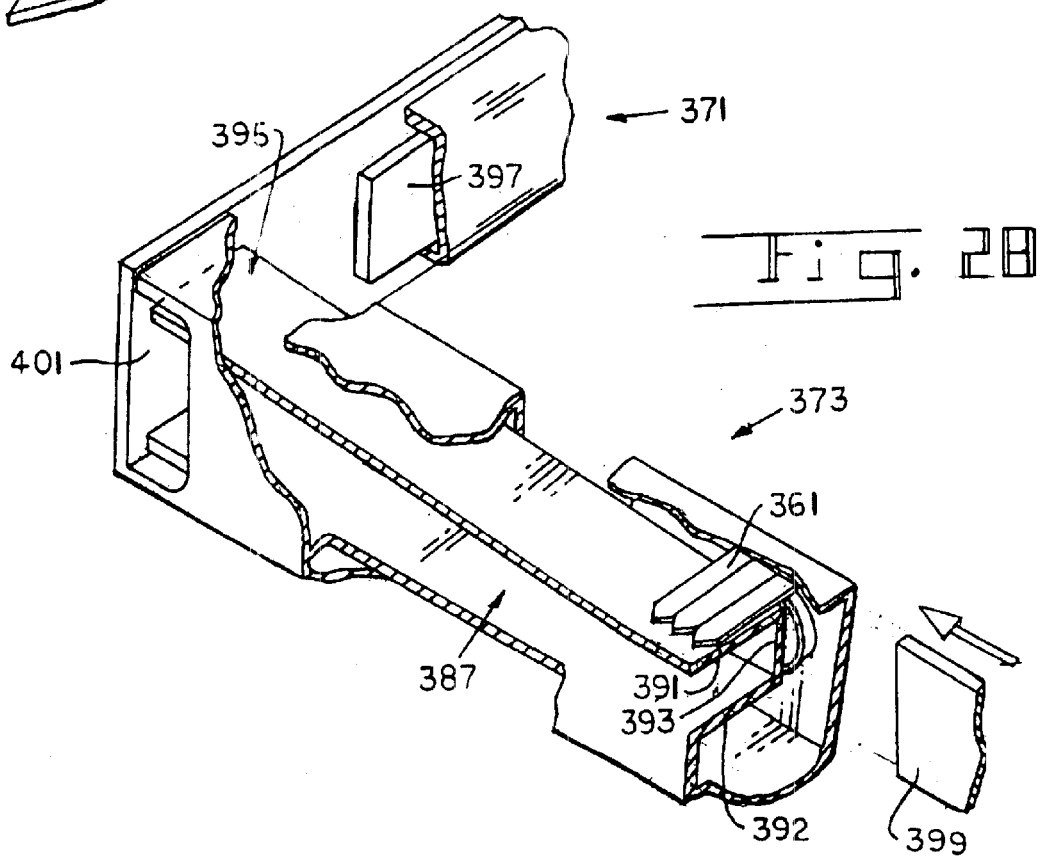

COMPRESSION BONE STAPLE, APPARATUS AND METHOD

This is a continuation of application Ser. No. 09/500,060, filed Feb. 8, 2000, now U.S. Pat. No. 6,348,054, which is a continuation-in-part of application Ser. No. 09/299,285, filed Apr. 26, 1999, now U.S. Pat. No. 6,059,787.

BACKGROUND OF THE INVENTION

1. Field of the Invention

The present invention relates to devices and techniques for securing bone segments across a fracture site, and more particularly relates to a bone stapling method and apparatus for achieving compression between segments.

2. Description of the Prior Art

In treating a bone fracture it is common practice to fasten one bone segment to the other so as to stabilize and immobilize them for the duration of the bone consolidation process. Thus there is the technique of internal fixation or direct mechanical fastening of the bone segments.

Traditionally, fixation has been accomplished by variety of apparatus and techniques, the more common involving the use of metallic fastening devices such as screws, connector plates (secured to the bone by screws), pins and clips. These methods invariably involve the drilling of screw holes in the bone and the use of related equipment such as drill hole templates.

Conventional U-shaped clips have also been used, the clip legs being installed one each in holes in the opposing bone segments. The rigid structure of such clips, like the other fixation devices mentioned above, provide rigid immobilization of the fracture zone. Such devices also served to maintain the distance between segments, which was found however, among other things, to hinder compression induced by contractions of skeletal muscles in some cases, and prevent the establishment of compressive force between the bone segments which is favorable to bone consolidation or knitting. In this regard the concept of creating dynamic compressive force across an osteotomy or bone fracture site has become well recognized as a technique to promote primary bone healing, i.e. consolidation that is faster and of better quality.

Thus there has evolved a number of fastening devices such as clips and the like, designed to deliver compression. Accordingly in U.S. Pat. No. 3,939,294 there is provided a clasp or clip of spring material having a pair of spaced-apart, inwardly inclined legs connected by a Z-shaped upper portion. Sloped holes are drilled in adjoining bone segments and tools are used to manipulate and install one leg, and then the other leg is pulled toward the other hole, spreading the Z-shaped elastic portion, and then inserted in the other hole. Unfortunately this method requires the drilling of specially sloped holes, involves multiple steps and is time-consuming, and like the conventional rigid fastening techniques, requires relatively large surgical opening. Also, the manual installation of the clip using hemostats and the like is difficult, requires meticulous skill and handling.

In U.S. Pat. No. 4,838,254 the legs of a pair of metallic clips are inserted in pairs of specially angled bores in respective opposing bone segments The exposed tops of the two installed clips then serve as fastening heads for a spring that is connected between the clips.

In U.S. Pat. No. 4,841,960 the disclosed "compression" clip is essentially a clip with opposing legs that are installed in pre-drilled holes and features a crimpable web that joins the top ends of the legs. A crimping tool is used to crimp the web in an effort to set up compression between the embedded legs.

U.S. Pat. No. 4,852,558 also requires manual installation of separate legs in predrilled holes, the tops of the install legs then being interconnected with a ratchet mechanism which must be operated to draw the legs together. This design appears inherently limited regarding adjustability and maintenance of constant pressure. In U.S. Pat. No. 5,660,188 the two legs of a clip must also be installed in pre-drilled holes. The clip has a bridge of two side-by-side crimpable elements, and the jaws of a crimping tool must be used on the embedded clip to deformingly spread apart these elements, causing the legs to draw to each other. The foregoing techniques involving crimpable clips all appear to be imprecise in setting up suitable compressive forces, require hole drilling and related problems, and do not lend themselves to minimizing the size of the surgical opening.

In view of the limitations of the afore-mentioned methods, stapling has been looked to as a potentially quick and effective way for fastening bone segments, and as a way to produce compression. Thus in U.S. Pat. Nos. 5,053,038 and 5,662,655 "compression" staples are applied to the bone by a powered stapler. These staples have legs shaped with beveled ends and/or have divergent legs that will be forced apart from each other during implantation, which flexes springy upper parts of the legs thereby tending to set up compression. Unfortunately there is concern for trauma to the bone due to driving of the compound-shaped legs into the bone mass, and there is little apparent precision in establishing the desired compressive forces.

In view of the foregoing it is a general object of the present invention to provide an improved method and for interosseous fastening.

A more particular object is to provide quick and simple, yet effective method for fastening bone segments with compressive force between opposing bone ends.

Another object to provide such a method that minimizes the size of the required surgical opening and associated trauma.

A further object to provide a method of bone stapling that minimizes trauma to the bone tissue during implantation of the staple legs.

Yet another object is to provide a method for stapling that maximizes the capability of establishing a dynamic compression level that is optimal for enhanced osseous healing.

A still further object is to provide simple, effective bone fixation technique that is relatively easy to learn and practice.

Another object is to provide for compression fixation in applications where other techniques would not work or would not deliver compression. For example, conventional fastening techniques for handling a "Jones" fracture, i.e. one that is transverse to the longitudinal extent of the bone segment, is difficult to address using conventional fastening techniques, however the present invention is particularly suitable to provide fastening for such fractures.

Still another object is to provide stapling apparatus and method in which there is enhanced selection capability regarding the level of the compressive forces to be imparted.

There are a number of advantages in exterior bone fixation techniques, where surgical incisions are not required and fasteners are applied through the skin; and thus it is yet another object of the invention to provide a bone stapling method that lends itself well to exterior bone fixation.

These and other objects of the present invention are achievable by way of the present invention of a bone stapling method and apparatus that uses a generally U-shaped staple having pair of spaced apart legs with sharp free ends and proximal ends interconnected by bridge that has at least one resilient curved portion, whereby spreading apart of the parallel legs lessens the curvature of the curved portions which brings the staple to a tensioned configuration in which one leg is resiliently urged towards the other. In a preferred embodiment it is seen that the bridge portion comprises a single bowed spring element, the curvature of which lies in a plane normal to the axes of the staple legs.

The novel fastening method involves first positioning the fractured ends of a first and a second bone segment in proximate, face-to-face relationship. The next step involves spreading apart the staple legs by a certain amount and holding the staple in the resultant tensioned configuration. The extent to which the staple legs are separated can be varied in one preferred embodiment of the invention, the induced compressive forces between the legs being proportional to the amount of displacement of the legs as the bowed portion is moved through range of motion in which elastic behavior is exhibited. In this regard it should be evident that herein lies one of the advantages of the present invention, i.e. the capability of selecting the optimal compressive force for an application by spreading apart the staple legs by a predetermined amount.

Next, as the staple is held in its tensioned configuration, it is positioned with it sharp ends forward and aligned respectively with surfaces of one bone segments and the other. Finally the positioned staple, while maintained in its tensioned configuration, is driven into the bone by percussive force, such quick application being provided by a conventional air-powered striker of a stapler according to the present invention, or by a manually stuck staple applicator according to the invention. The embedded staple legs will cause the opposing bone faces to be pressed into each other with a predetermined amount of force.

Such stapling method lends itself advantageously to a staple with a relatively narrow profile, wherein apparatus according to the present invention include a staple applicator having within its housing means for supporting the staple and guiding its movement with legs pointed ends forwardly disposed, and adapted to receive the staple in its initial un-tensioned configuration engaging its legs and spreading them apart by certain amount and holding the staple in its tensioned configuration adjacent the front end of the housing, for ejection therefrom. One embodiment, of several, uses opposing first and second grooves for engaging the staple legs and means for adjustably moving one groove from the other. Another embodiment employs grooves that diverge to spread the staple legs as a staple is advanced there-along. Ejection means mounted for longitudinal movement in the housing has a front end adapted to strike the rear of the tensioned staple with percussive force which is provided by air power or electrical power in preferred embodiments.

The invention also includes a staple applicator that is adapted for being manually driven.

Another related bone stapling method for compressively securing adjoining bone segments uses a resilient metallic staple that has legs with an initial convergent configuration with respect to each other, and the legs are resiliently extendible into parallel relationship, in which configuration a predetermined amount of spring force will urge the legs towards their initial convergent orientation. This method includes holding the normally convergent staple in its legs-parallel configuration, positioning the so-tensioned staple with its sharp ends aligned respectively with adjacent bone surfaces; and then driving and embedding the legs of the tensioned staple in the bone segments and releasing the embedded staple, whereby the bone segments are joined, and opposing surfaces of the bone segments are caused to be pressed into engagement with each other with a certain amount of compressive force.

An applicator or tool for such a staple includes staple-engaging means on the front end of the applicator body. Opposing jaws support the staple in a pointed-ends forward position against lateral and rearward movement, and engage inside surfaces of the convergent legs, the jaws being adapted for adjustable movement apart to cause the legs to rotate to a generally parallel orientation. Thus supported on the front end of the tool, the staple can be aligned with the bone segments, and the rear end of the tool stuck with a percussive force to cause the staple legs to be embedded into the bone segments.

Another applicator according to the present invention has a trigger-controlled air-powered staple-driving mechanism, and has a staple feeding mechanism including ramp means that is shaped to receive and support a staple in its initial configuration on one end of said ramp means, the configuration of the ramp means gradually changing to a shape that will hold the staple with its legs generally parallel with each other. Thus the staple can be slidably pushed along the ramp means in a lateral direction, i.e. normal to the plane in which the staple legs and bridge portion lie, to bring it to a terminal position along the ramp means, in which position the rear of the tensioned staple can be struck by the front end of a powered striker.

BRIEF DESCRIPTION OF THE DRAWINGS

FIG. 6 is a partial, perspective enlarged view of the front end of the staple applicator of FIG. 5;

FIG. 7 is a sectional view taken long the line 7—7 of FIG. 6;

FIG. 8 is sectional view taken long the line 8—8 of FIG. 6;

FIG. 9 is an enlarged, partial perspective view of the front portion of a variant of a staple applicator according to the present invention;

FIG. 10 is an enlarged, partial perspective view of the front portion of another variant of a staple applicator according to the present invention;

FIG. 11 is a top plan view of a manually powered stapler according to the present invention;

FIG. 12 is a partial, enlarged perspective view of the front portion of the staple applicator of FIG. 11;

FIG. 13 is a sectional view taken along the line 13—13 of FIG. 12;

FIG. 14 is a perspective view of another variant of a compressive staple according to the present invention, wherein the staple legs have a convergent orientation with respect to each other;

FIG. 15 is a side elevational view of the staple of FIG. 14;

FIG. 16 is a top plan view of a staple applicator according to the present invention;

FIG. 17 is an enlarged, partial perspective view of the front end of the applicator of FIG. 16;

FIG. 18 is an enlarged partial, side elevational, partially sectional view illustrating the mounting of a staple on the front end of the staple applicator of FIG. 16;

FIG. 26 is a perspective view of another variant of another compression staple similar to the staple of FIG. 1, and adapted for use with a staple-feeding magazine or cartridge;

FIG. 27 is a front end elevational view of the staple of FIG. 26; and

FIG. 28 is a partial sectional perspective view, with parts broken away for the sake of clarity, illustrating a magazine or cartridge for feeding the staple of FIG. 26 to a powered staple applicator.

DETAILED DESCRIPTION OF THE INVENTION

Figure 1:
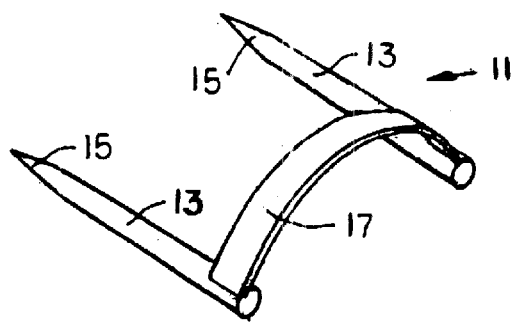
FIG. 1 is perspective view of a preferred embodiment of a compression staple according to the present invention.
Figure 3:
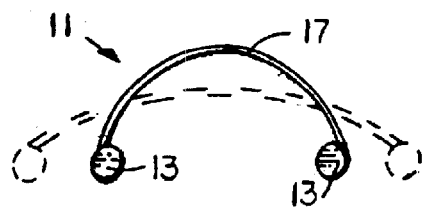
FIG. 3 is a rear end elevational view of the staple of FIG. 1.
Figure 2:
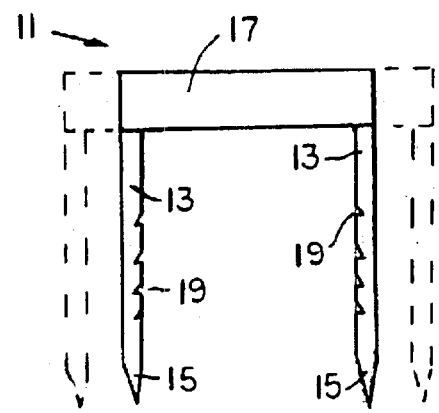
FIG. 2 is top plan view of the embodiment of the staple of FIG. 1.

Referring now the drawings, FIGS. 1–3 show that a preferred embodiment of a compression staple 11 according to the present invention has a pair of legs 13 with sharp front ends 15 and a bridge 17 that interconnects the rear end portions of legs 13. Staple 11 is fabricated of a surgical grade, bio-compatible metal, such as stainless steel, titanium alloy or other suitable alloy. Bridge 17 functions not only to hold legs 13 in approximate parallel relationship, but is selected to act as a spring by the flexing of its bow when the legs are spread apart as illustrated by the broken line image of FIGS. 2 and 3. This imparts an inward reacting force between the legs proportional to the degree of their displacement. It will be appreciated that the dimensions, gauge and curvature of bridge 17 are selected such that it can be flexed to a tensioned state that will deliver the compression requirements of the bone fixation to which staple 11 is to be applied.

It is preferred that the opposing inside surfaces of legs 13 are provided with serrations or barbs 19. In this regard it is noted that, inasmuch as the insides of legs 13 will be pressed against bone mass when they are embedded in a manner to be described, the size of such serrations or barbs can be advantageously minimized, which minimizes trauma to the bone tissue during their implantation.

Figure 4:
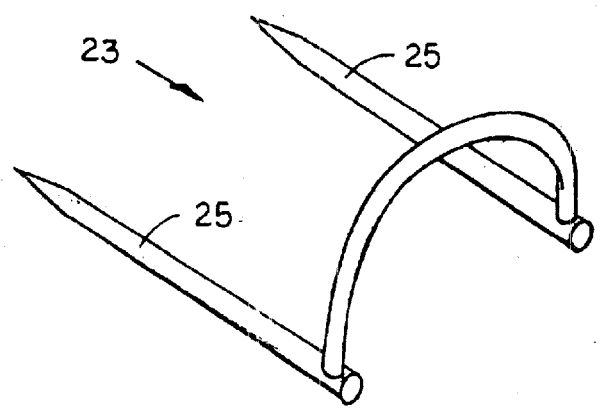
FIG. 4 is a perspective view of variant of a staple according to the present invention.

It will be evident that there can be several variations of compression staples according to the principles of the invention. For example, staple legs can have various cross sectional configurations, including diamond-shaped, square, triangular and rectangular. FIG. 4 shows a variant 23 of a staple according to the present invention, having legs 25. It is formed from metal rod having suitable strength and spring properties. It is also contemplated under the invention that the curvature of the bridge can take other forms than the single bow shown, and would include, among others a generally V-shape and a shape with double 90 degree bends.

Figure 5:
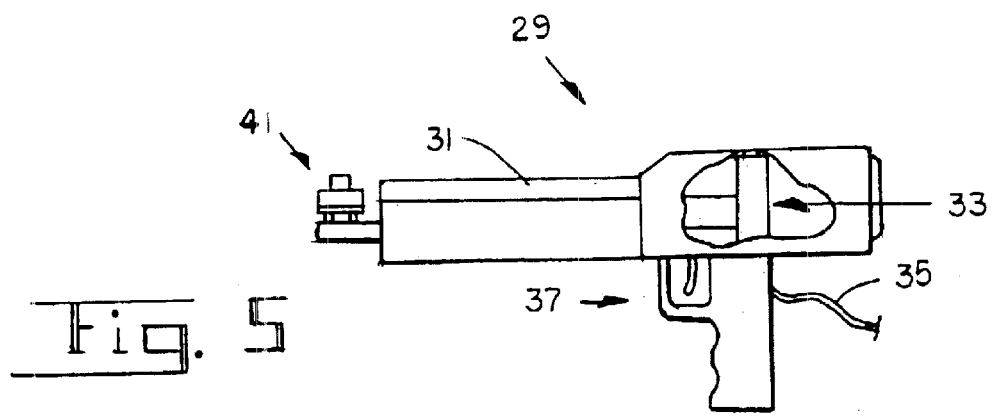
FIG. 5 is an elevational view of staple applicator according to the present invention, with parts broken away for the sake of clarity.

FIG. 5 shows an air-powered staple applicator 29 for applying staple 11, and it includes main body 31, a conventional air piston assembly 33 within body 31, air supply line 35 and a pistol grip and trigger assembly 37 for holding the stapler and for controlling the air-powered operation of the staple head 41, to be described hereinafter.

As FIG. 6 illustrates, the staple head 41 features an adjustable staple mount 43 that includes lower head 45 which is a forward extension of body 31, and upper head 47. A pair of parallel guide rods 51, affixed to lower head 45 and extending upwardly therefrom, slidably engage twin bores 53 in the upper head 47 so as to guide the upper head in vertical motion relative to the lower head 45. A screw jack assembly drives the upper head and includes thrust screw 55 that engages the threaded bore 57 in lower head 45. FIG. 7 best illustrates the screw jack assembly and shows turn knob 59 that has a socket for receiving a tool such as an Allen wrench for rotating the knob 59. FIGS. 6 and 7 also show a longitudinally extending groove 65 on the lower head 45 and a corresponding parallel groove 63 on the movable upper head 47, these grooves being shaped to cradle the opposing sides of staple legs 13, and the knob can be operated to set the spacing between grooves to allow staple 11, in its initial un-tensioned configuration, to be mounted thereon as illustrated.

In a preferred embodiment, vertically extending gradations are provided at 67 on a forward surface of body 31, adjacent the movable rear end of upper head 45, so as to gauge the displacement of the staple legs when the invention is operated in a manner to be described below.

As FIGS. 6 and 7 and 8 also show, staple applicator 29 includes mechanism for driving a staple forwardly from the staple head 41, and includes longitudinally extending striker member 69 that is slidably mounted to grooves 71 and 73 for longitudinal movement, and the rear portion (not shown), is connected to the air piston assembly, and spring means (not shown) will hold the striker in an initial rearward position as illustrated in FIG. 6. Striker member 69 has front surface 75 that is adapted, as best shown in FIG. 7, to impact the rear legs of the staple bridge 17 when the striker member 69 is propelled to its forward position shown by the phantom lines in FIG. 6.

In the operation of staple applicator 29 for osteosynthesis, a staple 11 is mounted to the staple mount 43 which is operated to bring the staple to the desired tensioned configuration. Then bone segments are brought together by manual or mechanical manipulation as close as possible and aligned with each other. The stapler head 41 can then be positioned with its legs straddling the fracture line, and sharp ends 15 adjacent the surfaces of the bone segments. The stapler trigger can then be operated to cause the striker to drive the legs of the tensioned staple into the bone segments.

There is a variant of a staple applicator according to the invention that is identical to the embodiment of FIGS. 6 and 7, except that it has a striker member 69a is designed to engage the rear ends of staple legs 13 instead of the rear edge of the staple bridge 17. Thus the sectional view of FIG. 9 shows ends 79 and 80 that are adapted to strike respectively the upper and lower rear ends of staple legs 13, of a staple 11 supported in tensioned configuration. It is contemplated under the invention that strikers like striker 69a, with differently spaced ends 79 and 80 can be provided so that different sized staples can be accommodated.

FIG. 10 shows the forward portion 81 of another variant of a power stapler applicator according to the present invention, having a main body 82, an upper staple guide 83 and lower staple guide 85. Opposing forward portions 87 of the guides are separated by a distance allowing it to hold staple 11 in tensioned configuration, and the rearward portions 89 will hold the staple in its initial configuration. The open-sided portions 91 allow a staple to be loaded by hand unto the staple guides. When the staple is pushed forwardly by hand from portion 89 to portion 87, the divergent portions 93 will cause the spreading apart of the staple legs, and thus a tensioned staple is positioned for ejection.

A striker member 95 has upper and lower edges 97 and 99 slidably engaged in slots 101 and 103 so as to mount the striker member for longitudinal movement. The striker front ends 105 and 107 will align with and abut the rear ends of a tensioned staple.

FIGS. 11, 12 and 13 show a variant 113 of the invention, whereby percussive force is delivered by hand using a suitable mallet. Here the body 115 has a rear portion 117 designed for being struck by a mallet, and staple holder 119 at its front end. FIGS. 12 and 13 show how the holder 119 includes lower portion 121 that has staple leg-receiving groove 129, and an adjustable upper part 135 with groove 137. FIG. 12 best shows how a dove-tail portion 141 of part 135 fits in a complementary slot for guiding vertical movement of part 135. Front surfaces 145 and 147 respectively of parts 121 and 135 are adapted to abut the rear ends of a staple mounted in grooves 137 and 129. A screw 153 for driving the part 135 has threads 157 that engage a threaded bore 159 in the movable part 135, and the knob 163 can be engaged by a suitable tool to rotate the screw 153.

In using tool 113 the sharp ends of a tensioned staple 11 can advantageously be precisely positioned on the target spots on the bone segments, then the tool end 117 struck with a mallet to implant the staple.

Referring now to FIGS. 14 and 15 there is shown in FIG. 14 another compressive staple 161 according to the invention that is fabricated of a suitable resilient metal, and features legs 163 and 165 that converge with respect to each other, and interconnect by a bridge 167. Staple 161 can also be made of a suitable resilient non-metallic bio-absorbable material.

FIG. 15 best shows how legs 163 and 165 each converge at a pre-selected angle Φ, with respect to parallel positions that the legs can be resiliently urged in a manner to be described hereinafter. It should be apparent that the material properties of the selected resilient material, the degree of convergence, and the dimensions and form of the staple will be selected by those with ordinary skill in the pertinent art so as to establish a certain force by which the parallel legs are urged to their convergent positions.

FIG. 16 shows one preferred embodiment of a bone-staple applicator 171 having a main body 173 with a rear end 175 adapted for being impacted by a force delivering instrument like a mallet. The front end 177 is designed to mount a staple 161 in its initial configuration and then move it to, and hold it in, a configuration where its legs are parallel. Thus it is seen in FIG. 17 that front end 177 has an upper jaw 181 that can be adjustably spaced from to a lower jaw 183 using a drive-screw mechanism similar to that used for the screw-driven spreadable parts 135 and 121 previously described above and shown in FIGS. 12 and 13. FIG. 17 shows how the upper jaw 181, and lower jaw 183 are shaped to mount a staple 161, the slots 187 and 189 in the respective jaws being sized to receive the staple bridge 167. A recessed portion 191 in the top of the jaw 181 is for supporting and stabilizing rearward portions of the upper staple leg 163, and there is a similarly recessed portion on the under-surface of the lower jaw 183 (not shown) for supporting the rearward part 196 of lower staple leg 165. The recessed portion 191 has a shelf 193 for engaging lower surfaces of leg 163, and opposing edges 195 can hold the staple against lateral movement while the ledge 197 is adapted to abut the rear edge of the staple leg.

Figure 19:
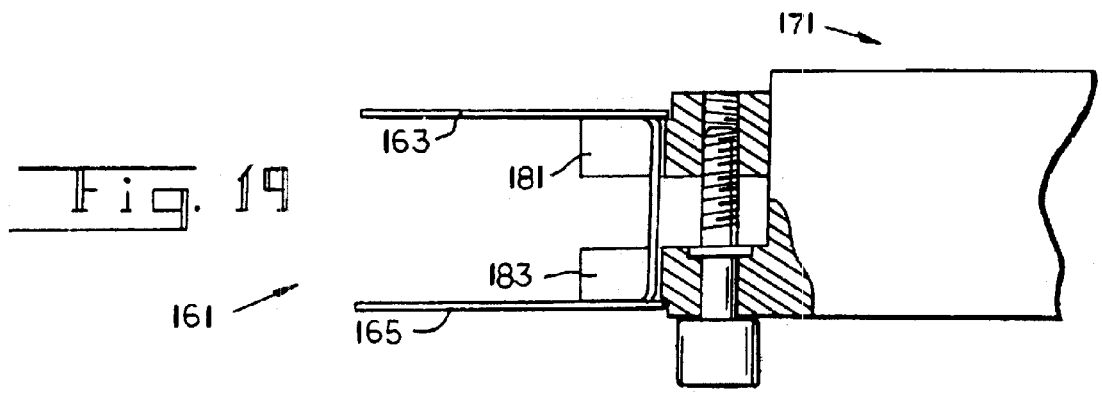
FIG. 19 is a view similar to FIG. 18 showing a staple supported with legs parallel.

FIG. 18 best shows how an untensioned staple 161 is first mounted within the grasp of the opposing recessed portions of the jaws 181 and 183, and it is noted how surfaces 193 and 194 engage inner surfaces 211 and 213 of opposing legs 163 and 165. It should be appreciated how the screw mechanism 217 can be operated to move apart the opposing jaws, causing the opposing legs to be pushed into parallel relationship, as illustrated in FIG. 19. When a staple 161 is thusly mounted on the applicator tool 171, it can be used much the same as the previously described device 113, to apply a tensioned staple 161 to adjoining bone segments. Note that the jaw surfaces 193 and 194 can be appropriately sloped to ensure that the legs will be pushed into parallelism.

Figure 20:
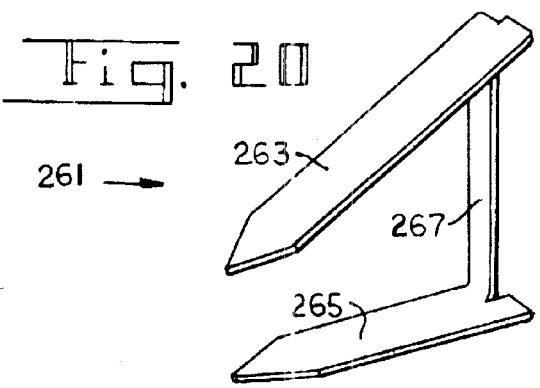
FIG. 20 is a perspective view of a convergent-legged staple that is adapted to be fed to a powered staple applicator.
Figure 21:
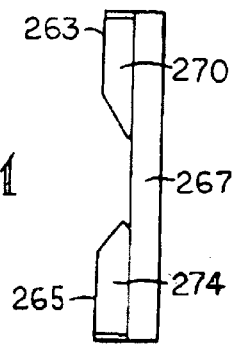
FIG. 21 is a rear elevational view of the staple of FIG. 20.
Figure 22:
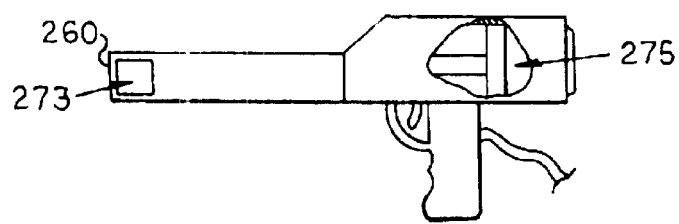
FIG. 22 is a side elevational view of another powered applicator according to the invention.

FIGS. 20 and 21 show another embodiment of a compression staple according to the present invention, i.e. the staple 261 which is particularly adapted for application by a powered applicator, for example an electrically powered or an air-powered staple applicator such as applicator 271 shown in FIG. 22, to be described. Like the previously described staple 161, the staple 261 is fabricated of a suitable resilient metal using conventional metal-working techniques. The staple legs 263 and 265 extend from the bridge portion 267 and converge at a predetermined angle. It is noted how legs 263 and 265 are wider than the bridge portion 267. The inside surfaces of the staple bridge and legs are adapted to slidably engage staple-feeding ramp structure, to be described. Furthermore, FIG. 21 best shows how this staple structure provides to one side of the bridge 267, opposing inside surfaces 270 and 274 respectively of legs 263 and 265, which can be advantageously engaged for slidable forward movement of the staple along parallel guide surfaces in the powered staple applicator 271, in a manner to be described.

Figure 23:
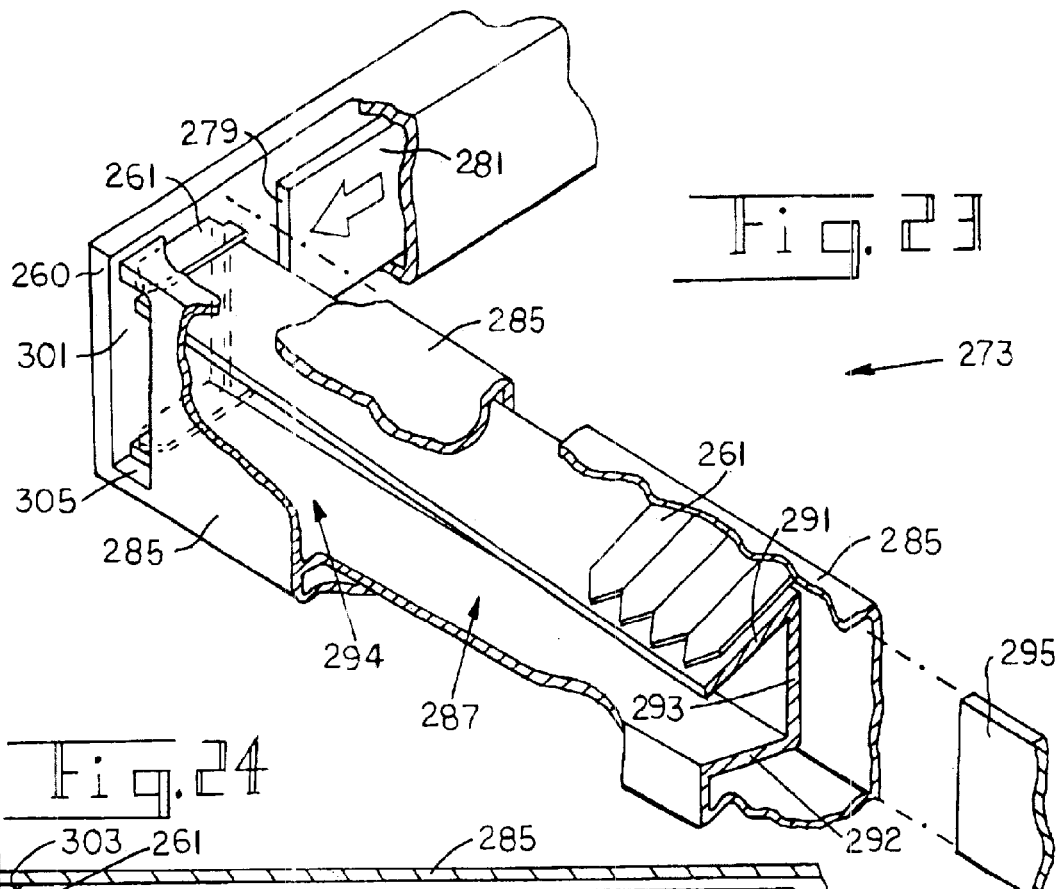
FIG. 23 is a perspective illustration showing means for feeding staples to the staple-driving means of the powered staple applicator shown in FIG. 22.

The trigger-controlled applicator 271, shown in FIG. 22, except for its forward end, is similar to the above-described applicator 29, and includes a piston assembly 275. FIG. 23 illustrates how at the forward end of the applicator 271, there is mounted a staple feeder 273 designed to supply and position staples for engagement by the front end 279 of a striker 281 that is connected to the piston assembly 275.

Figure 24:
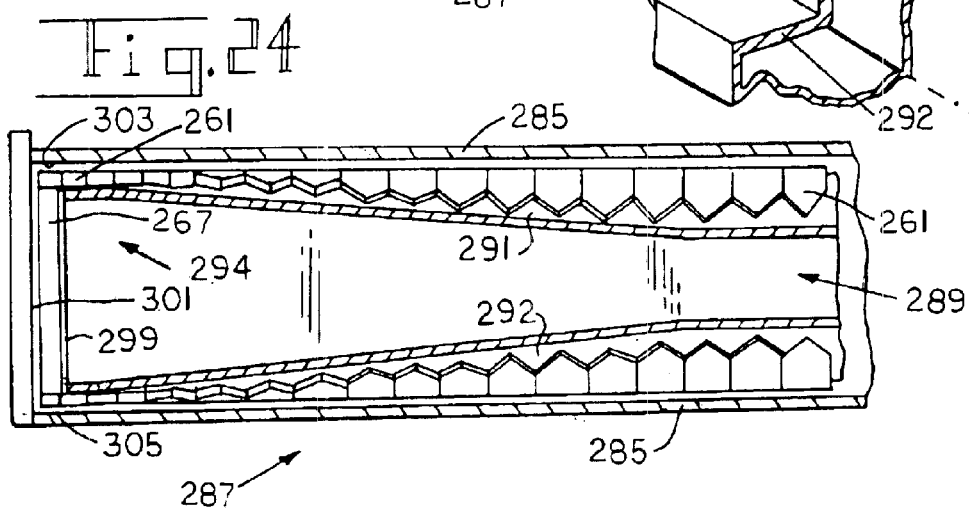
FIG. 24 is a partial, enlarged, partial sectional side view of staple-delivering ramp member of the applicator shown in FIG. 22.

FIG. 23 shows that the feeder 273 includes a housing 285 that is attached to a sidewall of the applicator and which supports a ramp member 287 that has a distal end 289 that is shaped to receive staples 261. The walls 291, 292 and 293 are shaped so as to be slidably embraced by a number of staples 261 in their relaxed, legs-convergent configurations. FIG. 24 also illustrates the ramp member 287 and shows how the ramp walls 291 and 292 vary from a convergent orientation at one ramp end to a generally parallel one at the opposite ramp end 294. FIG. 23 also illustrates that within the feeder housing 285 there is a spring-powered pusher 295, connected to a suitable conventional spring (not shown) for urging the pusher 295 against the rear side edges of a staple 261 mounted on the ramp member 287. Thus it can be appreciated how a staple 261, or several side-by-side staples 261, can be slidably pushed towards the end 294 of the ramp member.

Figure 25:
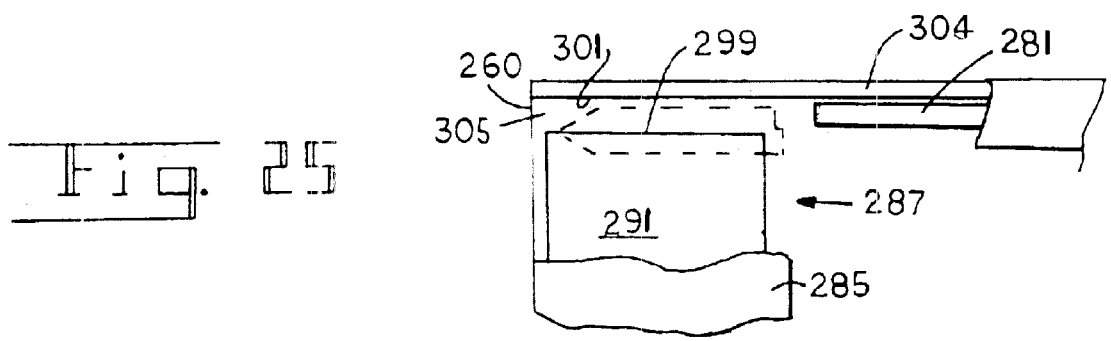
FIG. 25 is a schematic illustration of the staple-striking region of the staple feeding means of FIG. 23.

The enlarged view of FIG. 25 shows how the innermost end of the ramp member 287 has an end 299 that is spaced from a guiding surface 301 of applicator wall 304. Surfaces 301 and the opposing upper and lower surfaces 303 and 305 form a channel as FIG. 24 shows, for receiving the striker 281. FIG. 25 shows in broken lines a tensioned staple 261 in position for being driven by the striker 281. Note that the bridge member 267 is spaced within the above-mentioned channel, clear of the end of the ramp member 287, the staple being supported by virtue of the staple leg surfaces 270 and 274 (FIG. 21) engaging the ramp member. Thus the striker front end 279 is aligned with the rear end of staple bridge portion 267.

In operation of applicator 271 it is supported with its front end in close proximity to the relevant bone segments, and with the pointed ends of the staple appropriately aligned therewith. Pulling the trigger will cause the striker end 279 to impact the staple bridge and propel the staple forwardly as the staple legs are held generally parallel by sliding engagement with the generally parallel surfaces of the ramp member 287 during ejection.

The striker will have a stroke sufficient to cause the legs, in their parallel configuration, to be embedded in the bone tissue. The striker will return to its initial position rearward of the ramp member. Then spring force will cause another staple to be positioned in the ejection channel.

Although FIGS. 22 and 23 show the feeder 273 connected adjacent the front end 260 of the applicator, it should be appreciated that in some cases it is desirable that the feeder 273 attaches to the applicator 271 at a location spaced a greater distance to the rear of the front 260. In such cases the ramp walls 291 and 292 in the region of wall 301 are elongated forwardly as necessary to provide guide surfaces for the staple, and the stroke of the striker 281 is increased accordingly.

FIGS. 26 and 27 illustrate yet another variant 361 of the compression staple 11 described above (FIG. 1), and has generally parallel legs 363 and 365 and resilient bridge 367. This configuration provides opposing surfaces 370 and 374, best shown in FIG. 27, that are adapted to engage parallel guide surfaces when the staple 361 is propelled from a powered staple applicator 371, to be described. In FIG. 27 the tensioned configuration of staple 361 in shown in broken lines.

FIG. 28 shows a feeder 373 which is constructed similarly to the above-described feeder 273, except that the ramp member 387 is adapted to handle the staple 361. Thus the ramp walls 391 and 392 provide parallel surfaces for engaging inside surfaces of the staple legs and the wall 393 slidably abuts the wall 393.

The distal end of the ramp 387 receives staples 361 in their untensioned condition, and the walls 391 and 392 gradually diverge from each other such that at the other end 395 of the ramp, a staple 361 will be supported in a legs-parallel tensioned configuration. A spring-powered pusher 399 is adapted to urge a number of nested staples 361 towards the end 395 of the ramp.

The ramp end 395 is spaced a predetermined distance from the guide surface 401 and provides surfaces that engage the opposing surfaces 370 and 374 of staple 361. Thus the rear of a tensioned staple can be struck by the striker 397 and ejected from the applicator.

While particular embodiments of the invention have been described, it should be understood that the invention is not limited thereto, and includes other variants and modifications that will readily occur to those persons of ordinary skill in the art, given the benefit of this disclosure. Thus it is intended that the invention be given its full scope and breath as defined in the claims which follow.

What is claimed is:

1. A compression staple for fastening a first bone segment to a second bone segment, said staple comprised of a resilient material and having a generally U-shaped configuration, and comprising:

a) first and second spaced-apart longitudinally extending legs with sharp free ends and proximal ends;

b) a bridge portion interconnecting the proximal ends of said legs; and wherein said legs have a convergent orientation, one to the other, and said legs are adapted to be resiliently held in a parallel orientation wherein said legs are urged toward their initial convergent orientation with a predetermined force, and wherein said legs are wider than said bridge portion.

2. A staple as defined in claim 1 wherein said bridge portion lies to one side of said legs and the other sides of said legs have opposing generally flat surfaces.

* * * * *